(12) United States Patent
Chabansky

(10) Patent No.: US 9,763,721 B2
(45) Date of Patent: *Sep. 19, 2017

(54) CEMENT MIXER AND BONE FILLER DEVICE

(71) Applicant: KYPHON SARL, Neuchatel (CH)

(72) Inventor: Bruce Chabansky, Palo Alto, CA (US)

(73) Assignee: Kyphon SÀRL, Neuchâtel (CH)

( * ) Notice: Subject to any disclaimer, the term of this patent is extended or adjusted under 35 U.S.C. 154(b) by 42 days.

This patent is subject to a terminal disclaimer.

(21) Appl. No.: 14/869,254

(22) Filed: Sep. 29, 2015

(65) Prior Publication Data

US 2016/0015443 A1 Jan. 21, 2016

Related U.S. Application Data

(63) Continuation of application No. 13/359,848, filed on Jan. 27, 2012, now Pat. No. 9,204,914.

(51) Int. Cl.
*A61B 17/88* (2006.01)
*B01F 13/00* (2006.01)
(Continued)

(52) U.S. Cl.
CPC ...... *A61B 17/8833* (2013.01); *A61B 17/8816* (2013.01); *A61B 17/8822* (2013.01);
(Continued)

(58) Field of Classification Search
CPC ................. A61B 17/8833; A61B 17/8816
USPC ........ 222/386, 387; 366/130, 139, 189, 193; 604/82–85, 218, 225–226, 229; 606/92–95
See application file for complete search history.

(56) References Cited

U.S. PATENT DOCUMENTS 3,534,734 A * 10/1970 Budreck ................. A61M 5/28
 604/194
3,618,603 A * 11/1971 Levenson ............... A61M 5/24
 604/229
(Continued)

FOREIGN PATENT DOCUMENTS

| EP | 1466572 A2 | 10/2004 |
|---|---|---|
| JP | 2001218774 A | 8/2001 |
| WO | 2009105905 A1 | 9/2009 |

OTHER PUBLICATIONS

International Search Report and Written Opinion for PCT/US2013/022859 the counterpart application mailed on May 15, 2013.

*Primary Examiner* — Abbas Rashid

(57) ABSTRACT

An apparatus and method for mixing and dispensing bone cement is provided. The apparatus includes a mixing vessel for mixing bone cement attached to a syringe body. The syringe body having a lumen that is connected to the mixing vessel by a passageway between the mixing vessel and the lumen of the syringe body. A separator is provided between the mixing vessel and the syringe body and includes an orifice therein so that when the opening in the separator is misaligned with the lumen the passageway is blocked and when aligned the passageway is continuous with the lumen so that bone cement can pass into the syringe body. A plunger is provided and is slideably movable along the longitudinal axis of the syringe body so as to advance the bone cement out of the distal end of the syringe.

20 Claims, 4 Drawing Sheets

(51) Int. Cl.
 *B01F 15/00* (2006.01)
 *B01F 15/02* (2006.01)
(52) U.S. Cl.
 CPC .......... *A61B 17/8825* (2013.01); *B01F 13/00* (2013.01); *B01F 13/002* (2013.01); *B01F 15/00506* (2013.01); *B01F 15/0267* (2013.01); *A61B 2017/8838* (2013.01)

(56) References Cited

U.S. PATENT DOCUMENTS

| | | | |
|---|---|---|---|
| 5,085,638 A * | 2/1992 | Farbstein | A61M 5/322 128/919 |
| 5,114,405 A * | 5/1992 | Winter | A61M 5/5013 604/110 |
| 5,149,323 A * | 9/1992 | Colonna | A61M 5/5066 604/110 |
| 5,156,606 A * | 10/1992 | Chin | A61B 17/1628 606/100 |
| 5,320,603 A * | 6/1994 | Vetter | A61M 5/284 604/416 |
| 5,368,386 A | 11/1994 | Murray | |
| 5,383,864 A * | 1/1995 | van den Heuvel | A61J 1/062 604/202 |
| 5,496,285 A * | 3/1996 | Schumacher | A61M 5/31511 604/218 |
| 5,514,135 A | 5/1996 | Earle | |
| 5,558,136 A | 9/1996 | Orrico | |
| 5,674,195 A * | 10/1997 | Truthan | A61M 5/31596 604/187 |
| 6,083,229 A | 7/2000 | Constantz et al. | |
| 6,149,655 A | 11/2000 | Constantz et al. | |
| 6,767,335 B1 * | 7/2004 | Helg | A61M 5/322 604/110 |
| 7,744,270 B2 | 6/2010 | Plishka et al. | |
| 7,946,417 B2 | 5/2011 | Plishka et al. | |
| 8,021,037 B2 | 9/2011 | Krueger et al. | |
| 2006/0189958 A1 | 8/2006 | Talton et al. | |
| 2008/0065027 A1 * | 3/2008 | Sharp | A61M 5/5013 604/220 |
| 2010/0292672 A1 * | 11/2010 | Lee | A61M 5/31596 604/518 |

* cited by examiner

CEMENT MIXER AND BONE FILLER DEVICE

CROSS-REFERENCE TO RELATED APPLICATIONS

This application is a continuation of U.S. patent application Ser. No. 13/359,848, filed Jan. 27, 2012, which is hereby incorporated by reference herein in its entirety.

TECHNICAL FIELD

The present invention relates to devices and methods for mixing curable materials for use with stabilizing bone structures. More particularly, it relates to devices, systems and methods for mixing the components that form the curable materials.

BACKGROUND

Vertebral compression fracture (VCF) can occur when a vertebral body is too weak to support a load and the spine collapses. A VCF may cause the spine to shorten, leading to spinal deformities and altering spinal biomechanics. Collapse may result in thoracic and lumbar spinal deformity and is often seen in elderly people. The spinal deformity, commonly known as a Dowager's Hump, is also referred to as kyphosis. Several causes can lead to a VCF, including osteoporosis, cancer or a traumatic incident, such as a fall or car accident.

A treatment for a VCF can involve injecting a material into vertebra, either at low or high pressure. Optionally, a surgical balloon can first be inserted into a vertebra and expanded to restore a collapsed vertebra to its original shape. A material can then be inserted into the restored vertebra, which, upon hardening, can maintain the original shape of the vertebra. The technique of inserting a material into a cavity, such as a collapsed vertebra, can also be used to treat other medical conditions, for example, in knee or hand joints.

Surgeons commonly use bone cement in order to fill voids in bone. It is desirable to use bone cement, such as an adhesive bone cement, to hold small bone fragments in place to allow for healing, when methods such as traditional plate and screw methods of reattachment are not feasible. Only a small amount of bone cement may be required to fill small gaps between the bone fragments in order to glue the fragments together. For example, volumes of cement under one cubic centimeter may be used. In such applications, the cement material may be delivered to the repair site through a delivery system, such as a syringe having a cannulated needle.

The bone cement may be a mixture of different ingredients, and, before applying the bone cement to a repair site, the cement may be prepared by mixing it in a bowl with a pestle. Prepared bone cements can have various viscosities, and some may have quite a high viscosity, with a consistency like a tacky paste. For example, typical adhesive bone cement may have a viscosity greater than 80 Pascal-seconds. The prepared bone cement can be transferred to the syringe through the opening in the proximal end of the syringe, which is made accessible by removing the plunger from the syringe.

The prepared cement material can be difficult to pour into the proximal end of an application syringe, especially when it has a high viscosity. Additionally, the opening at the proximal end of the syringe may be quite small, thus making the pouring of the bone cement into the syringe even more difficult. The pouring of the bone cement into the proximal end of the syringe can also be time consuming, which can be problematic when the curing time for the cement is relatively short. Furthermore, the material that is poured into the proximal end of the syringe can develop air pockets along the syringe barrel. Air pockets can detrimentally cause pressure spikes during injection of the cement. These pressure increases can cause filter pressing, where the liquid portion of the cement separates from the powder portion. This can result in the liquid being squeezed out of the syringe, leaving behind a dense mass of powder, which can jam the syringe.

SUMMARY

This application relates to an apparatus for mixing and delivering bone cement and a method for filling a cavity in a patient's body with bone cement. The apparatus includes a mixing vessel for mixing the first and second materials to prepare the bone cement for delivery. A syringe body is attached to the mixing vessel. The syringe body defines a lumen and a longitudinal axis extending from a proximal end to an oppositely disposed distal end of the syringe body. Each of the proximal and distal ends having an opening therein. The openings in the syringe body are alignable with the orifice in the mixing vessel so as to provide a passageway between the mixing vessel and the lumen of the syringe body. A separator is provided between the mixing vessel and the proximal end of the syringe body. The separator includes an orifice therein. The separator is configured to slide between a first position wherein the orifice of the separator substantially aligns with the orifice in the mixing vessel and the passageway to a second position wherein the opening in the separator is misaligned so as to block the passageway between said mixing vessel and the passageway. When the separator is in the first position, the bone cement is transferred from the mixing vessel through the lumen to a dispensing structure. A plunger is provided and is configured to fit into the opening in the passageway between said mixing vessel and the lumen of the syringe body. The plunger is slideably movable along the central axis toward the distal end of the syringe body to facilitate movement of the bone cement into the dispensing structure.

A kit including one or all of the components of the bone cement mixing apparatus is provide, such as for example, a disposable, peel-pack, pre-packed sterile devices. The kit can also be provided in a sterilized or in the alternative be provided in a sterilizable packaging. The kit includes, at least one of the following: syringe body, mixing vessel, separator, plunger, base and dispensing structures. The syringes and dispensing structures can be of various sizes, gauges and types depending on the particular application. One or all of the components of the bone cement mixing apparatus may be reusable and sterilizable. The bone mixing apparatus may be configured as a kit with multiple sized and configured components.

The method of using the apparatus includes attaching a mixing vessel to a syringe body including a lumen and defining a passageway. A separator is positioned in a second position, where its orifice is not aligned with the orifice of the mixing vessel. A base can be attached to provide an easier gripping surface for holding the apparatus. Bone cement materials are place inside mixing vessel and are mixed thoroughly with a spatula. Once bone cement materials are thoroughly mixed, the separator is shifted to the first position where its orifice is aligned with the orifice of the mixing vessel and then passageway. The spatula is used to push and guide the bone cement mixture into the syringe body. A plunger is placed into the passageway of the syringe body through the orifices of the separator and the mixing vessel and is pushed towards the distal end of the syringe body. The apparatus is flipped over so that the handle of the plunger rests on table or other surface. If a base was attached, it can now be removed. A dispensing structure is attached the syringe body. A force can be applied to flanges to push the bone cement material into the dispensing structure. A plurality of dispensing structures can be filled one after another as needed for the particular use.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
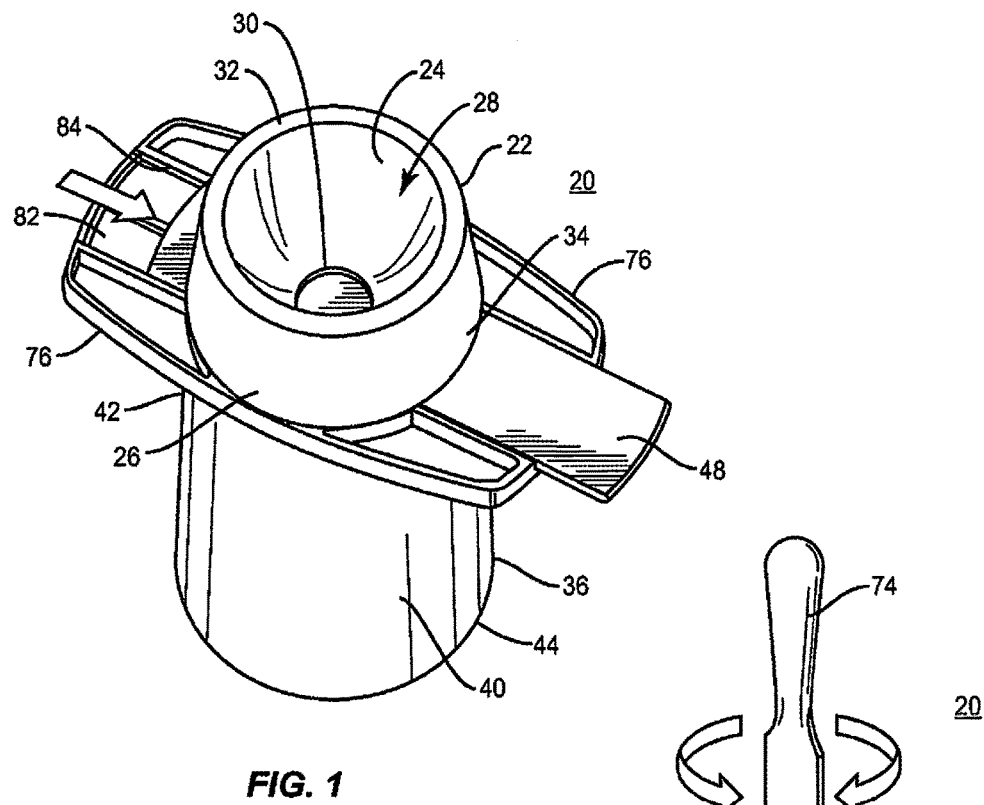
FIG. 1 is a perspective view of one particular embodiment of a system in accordance with the principles of the present disclosure.

An apparatus and method is described for injecting a material into a cavity in a patient's body. For illustrative purposes, the apparatus and method shall be described in the context of injecting a bone filling cement into a vertebra of a patient to treat kyphosis, although the apparatus and methods can be used to treat other conditions.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
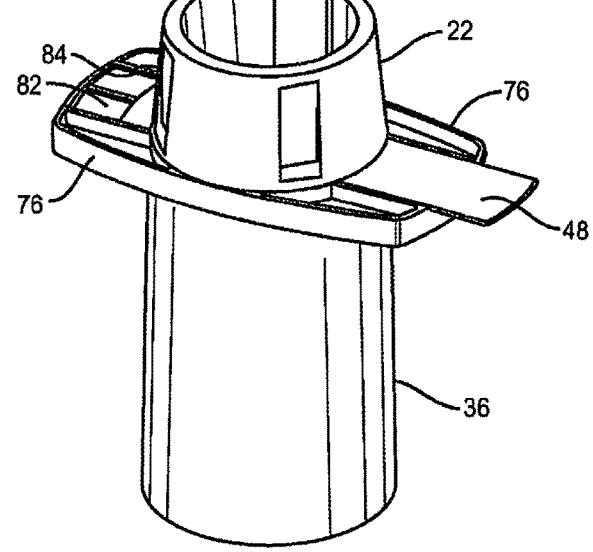
FIG. 2 is a perspective view of components system shown in FIG. 1 where the separator is in a second position.
Figure 3:
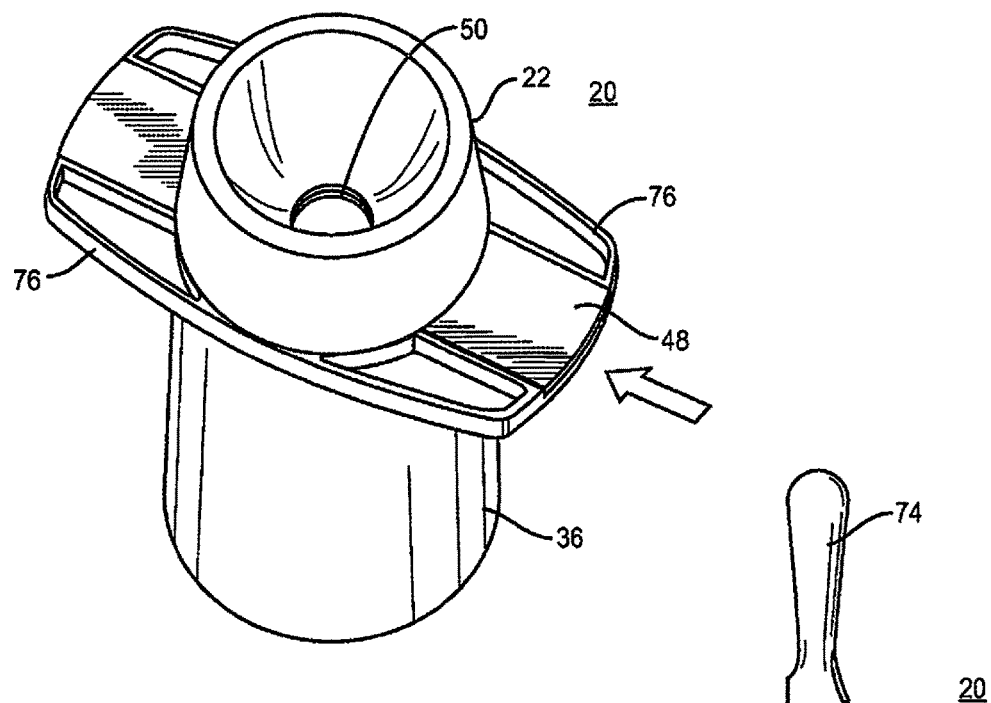
FIG. 3 is a perspective view of components of the system shown in FIG. 1 where the separator is in a first position.
Figure 4:
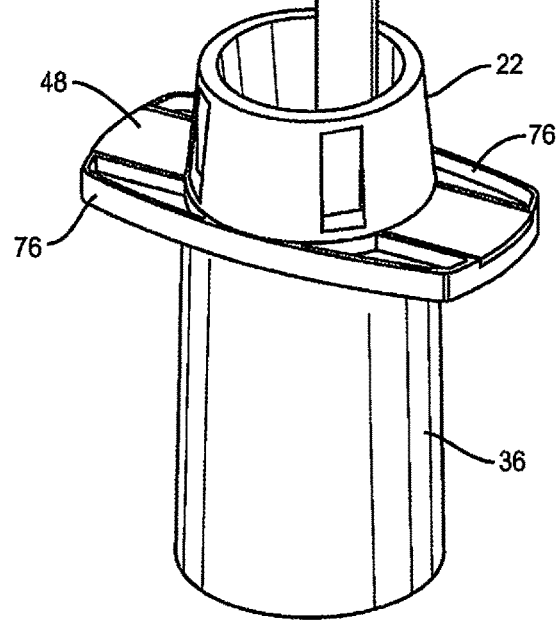
FIG. 4 is a perspective view of components of the system shown in FIG. 1 including a spatula.
Figure 5:
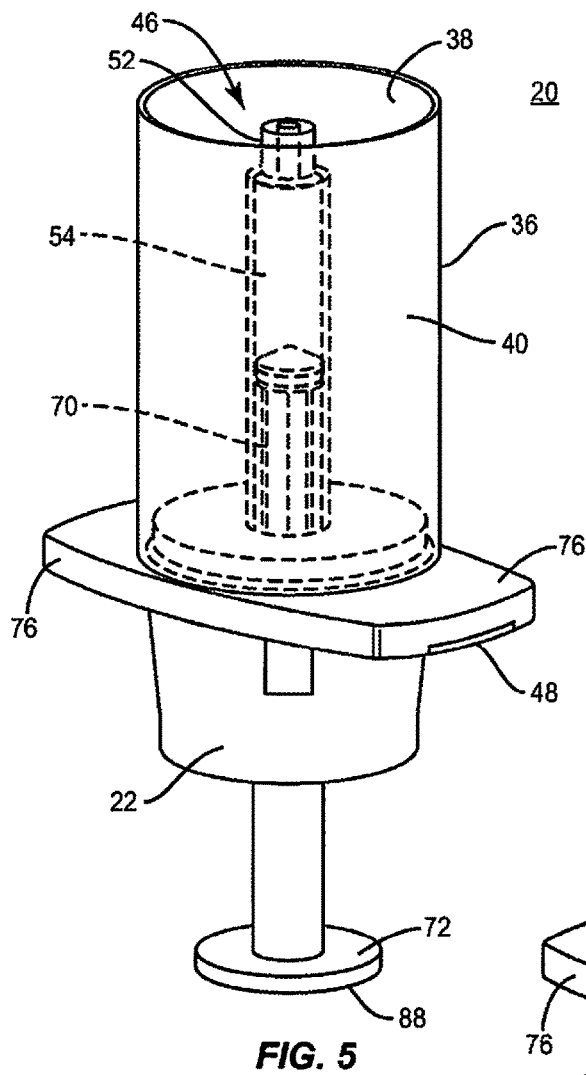
FIG. 5 is a perspective view of components of the system shown in FIG. 1 turned upside down and including the plunger.
Figure 6:
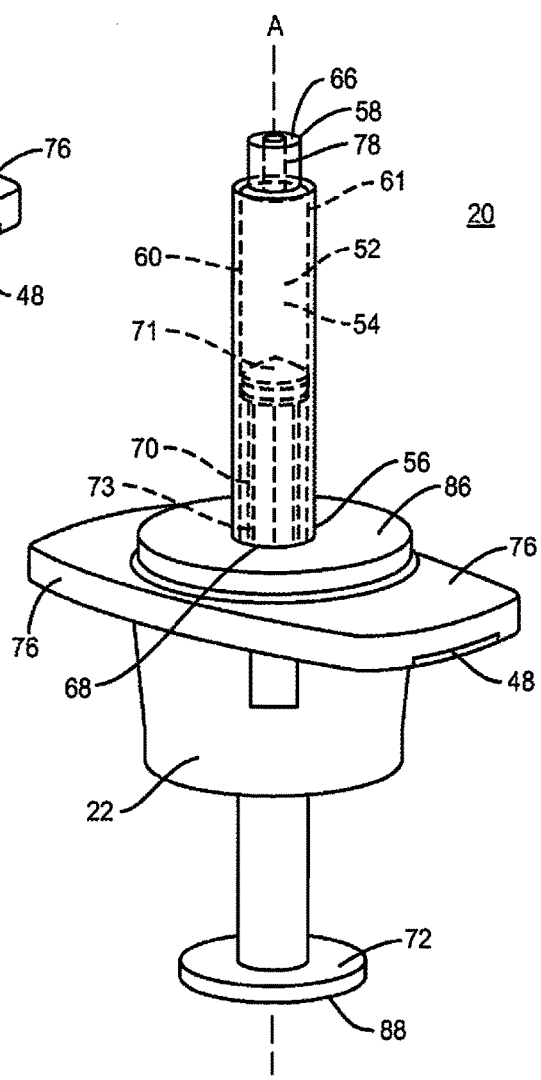
FIG. 6 is a perspective view of components of the system shown in FIG. 5.
Figure 7:
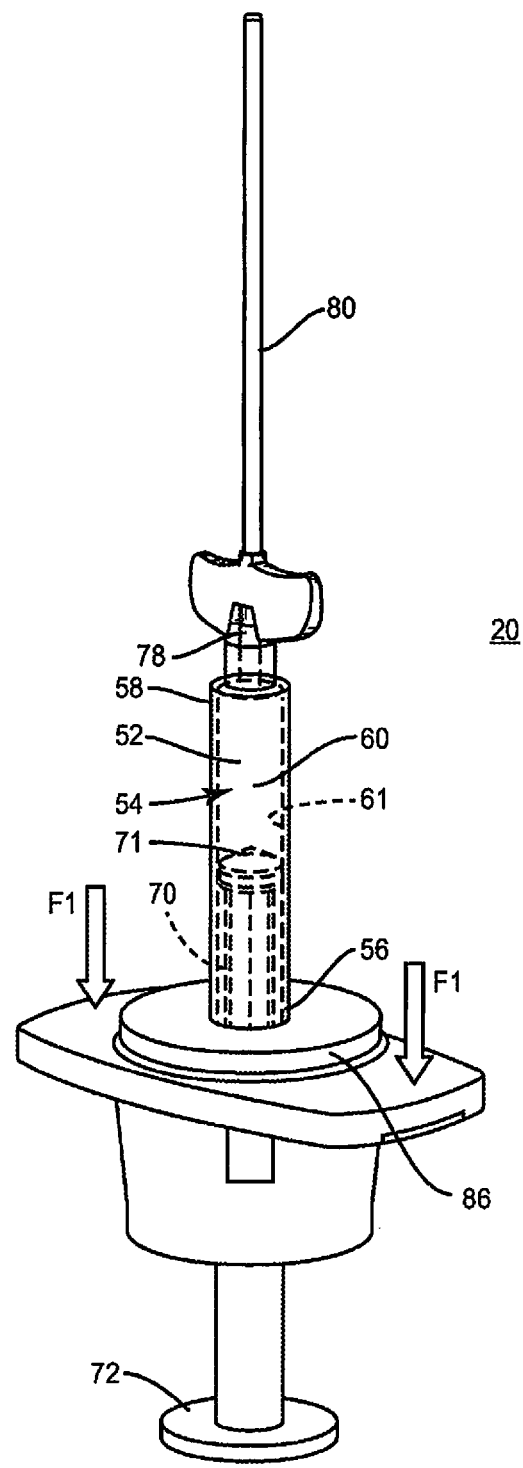
FIG. 7 is a perspective view of components of the system shown in FIG. 1 including a dispensing structure.

The following discussion includes a description of bone cement mixing apparatus and related methods of employing the apparatus in accordance with the principles of the present disclosure. Alternate embodiments are also disclosed. Reference will now be made in detail to the exemplary embodiments of the present disclosure, which are illustrated in the accompanying figures. Turning now to FIGS. 1-7, there is illustrated components of a bone cement mixing apparatus 20 in accordance with the principles of the present disclosure.

The components of bone cement mixing apparatus 20 can be fabricated from biologically acceptable materials suitable for medical applications, including metals, synthetic polymers, ceramics and bone material and/or their composites, depending on the particular application and/or preference of a medical practitioner. For example, the components of bone cement mixing system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglyclolide, polytyrosine carbonate, polycaroplaetohe and their combinations. Various components of bone cement mixing system 20 may have material composites, including the above materials, to achieve various desired characteristics such as strength, rigidity, elasticity, compliance, biomechanical performance, durability and radiolucency or imaging preference. The components of bone cement mixing system 20, individually or collectively, may also be fabricated from a heterogeneous material such as a combination of two or more of the above-described materials. The components of bone cement mixing system 20 may be monolithically formed, integrally connected or include fastening elements and/or instruments, as described herein.

In one embodiment, as shown in FIGS. 1-7, a bone cement mixing apparatus 20 is provided. Bone cement mixing apparatus 20 includes a mixing vessel 22 for mixing first and second materials to make bone cement. The first and second materials are used to fill bone cavities. Examples of cavity filling material include: bone cement (e.g., polymethyl methacrylate (PMMA) cement, ceramics); human bone graft (e.g., autograft, allograft); and synthetic derived bone substitutes (e.g., calcium sulfate, calcium phosphate, hydroxyapatite). Cavity filling materials can be supplemented with other therapeutic substances, e.g., antibiotics, growth factors and chemotherapeutic agents.

Bone cement mixing apparatus 20 includes a mixing vessel 22 having an inner surface 24 and an outer surface 26. Outer surface 26 extends between a first end 32 and a second end 34. Inner surface 24 forms a cavity, such as, for example, a bowl 28 for disposal and mixing of first and second materials. It is contemplated that mixing vessel 28 be round, oval, oblong, square, rectangular, polygonal, irregular, uniform, non-uniform, offset, staggered, tapered, consistent or variable, depending on the requirements of a particular application. Inner surface 24 includes an orifice 30 disposed at the second end 34. It is contemplated that orifice 30 be round, oval, oblong, square, rectangular, polygonal, irregular, uniform, non-uniform, offset, staggered, tapered, consistent or variable, depending on the requirements of a particular application.

Bowl 22 includes flanges 76 that extend outward from outer surface 26 of bowl 22 and transverse to central axis A. Flanges 76 provide a surface for applying a force F to advance a plunger 70 into the passageway, as discussed below. Flanges 76 include a channel 82 disposed therein. Channel 82 is configured as a track 84 accept disposal of separator 48, as discussed below. Flanges 76 include a coupling portion 86 configured to removably couple a base 36 discussed below to bowl 22.

A syringe body 52 is attached to second end 34 of bowl 22. Syringe body includes a proximal end 56 and a distal end 58. Syringe body 52 defines a chamber 54 extending between proximal end 56 and distal end 58 along a central axis A. It is contemplated that syringe body be round, oval, oblong, uniform, or tapered depending on the requirements of a particular application. Syringe 52 includes a lumen 60 disposed therein. Lumen 60 includes an inner surface 61. Lumen 60 extends through syringe body 52 from proximal end 56 to the oppositely disposed distal end 58 along axis A. Proximal end 56 includes an opening 66. Distal end includes 58 an opening 68. Openings 66 and 68 align with orifice 30 to provide a passageway between bowl 22 and lumen 60.

Distal end 56 further includes a coupling portion 78 adapted to attach to at least one dispensing structure 80. It is contemplated that dispensing structure 80 can be a cannula, a needle, a cannulated needle or a syringe needle. Second end 58 includes a coupling portion, not shown, for attachment and detachment of bowl 22. This allows for use of more then one or various sized syringe bodies or multiple bowls.

To allow for movement of the bone cement between bowl 22 and syringe body 52 a separator 48 is disposed between bowl 22 and syringe body 52. Separator 48 slides along track 84 disposed in channel 82. Movement of separator 48 allows separator to move from a first position to a second position along track 84. Separator 48 includes an orifice 50 that aligns with orifice 30 and passageway in its first position. Separator 48 is configured to slide between proximal end 56 of the syringe body 52 and bowl 22 from a first position wherein orifice 50 substantially aligns with orifice 30 to a second position wherein orifice 50 is misaligned with orifice 30 such that separator 48 blocks the passageway between bowl 22 and syringe body 52. It is contemplated that separator 48 be rectangular, round, oval, oblong, square, polygonal, irregular, uniform, non-uniform, offset, staggered, tapered, consistent or variable, depending on the requirements of a particular application.

To facilitate movement of the bone cement through the passageway, a plunger 70 is provided. Plunger 70 is configured to push the bone cement into and through lumen 60. Plunger 70 includes a proximal end 71 and a distal end 73. Distal end 71 is configured as a curved or radiused button or knob. Proximal end 73 of plunger 70 includes a handle 72. Plunger 70 is configured to fit through orifices 50 and 30 and slidably engages and extends through lumen 60 in syringe body 52 along central axis A towards distal end 58 of syringe body. Plunger 70 is sized for frictional engagement with inner surface 61 of lumen 60. Handle 72 includes a flat surface 88 that facilitates apparatus resting on a surface of a table. It is contemplated that flat surface 88 be rectangular, round, oval, oblong, square, polygonal, irregular, uniform, non-uniform, offset, staggered, tapered, consistent or variable, depending on the requirements of a particular application. Bone cement can be highly viscous and therefore requiring a significant force to be pushed into syringe body 52. After plunger 70 is inserted into orifices 50 and 30, apparatus 20 can be flipped over to rest on handle 72. By applying a downward force F on flanges 76, plunger 70 pushes the bone cement through lumen 60 into dispense 80.

To assist in holding apparatus 20 and for the protection of syringe body 52 a base 36 is attached to bowl 22. Base 36 extends between a first end 42 and a second end 44. Base 36 includes an inner surface 38 and an outer surface 40. It is contemplated that base 36 be round, oval, oblong, square, rectangular, polygonal, irregular, uniform, non-uniform, offset, staggered, tapered, consistent or variable, depending on the requirements of a particular application. Inner surface 38 defines a cavity 46 configured for disposal of syringe body 52. Base 36 is provided to allow the apparatus to stand upright on a surface without the end of the syringe body 52 touching the surface. Base 36 includes an opening 37 for viewing the syringe body 52 therein. In one embodiment, flanges 76 include a coupling portion 77 for attachment of base 36.

For mixing the bone cement materials, a detachable spatula 74 is provided. Spatula 74 can be detachably attached to base 36, mixing vessel 22 or other surface where practical.

In one embodiment, one or all of the components of the bone cement mixing apparatus are presented in a kit, such as for example, a disposable, peel-pack, pre-packed sterile devices. The kit can also be provided in a sterilized or in the alternative be provided in a sterilizable packaging. The kit includes, at least one of the following: syringe body, mixing vessel, separator, plunger, base and dispensing structures. The syringes and dispensing structures can be of various sizes, gauges and types depending on the particular application. One or all of the components of the bone cement mixing apparatus may be reusable and sterilizable. The bone mixing apparatus may be configured as a kit with multiple sized and configured components.

In operation, bowl 22 is attached to syringe body 52. Separator 48 is moved to its second position, where orifice 50 is misaligned with orifice 30 of mixing vessel 22. Base 36 can be attached to provide an easier gripping surface for holding apparatus 20. Bone cement materials are place inside bowl 22 and are mixed thoroughly with spatula 74. The approximate time of mixing is about 30 seconds. Once bone cement materials are thoroughly mixed, separator 48 is shifted to the first position where orifice 50 is aligned with orifice 30. Spatula 74 is used to push and guide bone cement mixture into syringe body 52. Time for this step is approximately 20-30 seconds. Plunger 70 is placed into syringe body 52 through orifices 50 and 30. Plunger 70 is pushed until the bone cement is close to opening 66. Apparatus 20 is flipped over so that handle 72 rests on table or other surface. If base 36 was attached, it can now be removed. A dispensing structure 80 is attached to proximal end 56 or syringe body 52. Apparatus 20 is now resting on handle 72 and a force F1 can be applied to flanges 76 to push bone cement material into dispensing structure 80. A plurality of dispensing structures 80 can be filled one after another as needed for the particular use. Apparatus 20 provides for quick transfer of the bone cement from bowl 22 to dispensing structure 80 thereby allowing for efficient use of time and bone cement. The present apparatus removes the step of having to pour the bone cement into the syringe body. The pouring of the cement allows for spills and wasted cement as well inefficient use of time. The initial dose of bone cement into dispensing structure can be discarded as it may contain air bubbles.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone cement mixing apparatus comprising:
    a mixing vessel comprising a body defining a cavity, the body comprising opposite first and second openings that are in communication with the cavity, the mixing vessel comprising a recessed track extending into an outer surface thereof;
    a syringe body comprising opposite proximal and distal ends, the syringe body being attached to the mixing vessel, the syringe body comprising a lumen and opposite first and second openings that are in communication with the lumen, the openings of the syringe body being concentric; and
    a separator slidably positioned in the track, the separator comprising an orifice, the separator being configured to slide between a first position wherein the orifice substantially aligns with the openings of the mixing vessel to a second position wherein the orifice is misaligned with the openings of the mixing vessel so as to block a passageway between the mixing vessel and the lumen.

2. The apparatus as recited in claim 1, further comprising a plunger that extends through the openings of the mixing vessel and into the lumen.

3. The apparatus as recited in claim 1, further comprising a plunger that extends through the openings of the mixing vessel and into the lumen, the plunger comprising a distal end having a maximum diameter that is less than that of the lumen.

4. The apparatus as recited in claim 1, wherein: the syringe body extends along a longitudinal axis between the proximal and distal ends; and the separator is configured to slide in opposite first and second directions along a transverse axis that extends perpendicular to the longitudinal axis.

5. The apparatus as recited in claim 1, wherein: the syringe body extends along a longitudinal axis between the proximal and distal ends; and the orifice is coaxial with the longitudinal axis when the separator is in the first position and the orifice is offset from the longitudinal axis when the separator is in the second position.

6. The apparatus as recited in claim 1, wherein side surfaces of the separator engage side surfaces of the track to prevent the separator from rotating relative to the mixing vessel.

7. The apparatus as recited in claim 1, wherein the separator is positioned between the openings of the mixing vessel and the openings of the syringe body when the separator is in the second position.

8. The apparatus as recited in claim 1, wherein the orifice is round.

9. The apparatus as recited in claim 1, wherein the orifice has a uniform radius of curvature.

10. A bone cement mixing apparatus comprising:
    a mixing vessel comprising a body defining a cavity, the body comprising opposite first and second openings that are in communication with the cavity, the mixing vessel comprising opposite first and second flanges that extend outwardly from the body, the flanges each comprising a recessed track extending into an outer surface thereof;
    a syringe body comprising opposite proximal and distal ends, the syringe body being attached to the mixing vessel, the syringe body comprising a lumen and opposite first and second openings that are in communication with the lumen; and
    a separator slidably positioned in the tracks, the separator comprising an orifice, the separator being configured to slide between a first position wherein the orifice substantially aligns with the openings of the mixing vessel to a second position wherein the orifice is misaligned with the openings of the mixing vessel so as to block a passageway between the mixing vessel and the lumen,
    wherein the syringe body extends along a longitudinal axis between the proximal and distal ends, the tracks extending along a transverse axis that is perpendicular to the longitudinal axis.

11. The apparatus as recited in claim 10, wherein end surfaces of the separator are flush with end surfaces of the flanges when the separator is in the first position and the end surfaces of the separator are spaced apart from the end surfaces of the flanges when the separator is in the second position.

12. The apparatus as recited in claim 10, further comprising a plunger that extends through the openings of the mixing vessel and into the lumen such that the plunger is movably positioned within the lumen.

13. The apparatus as recited in claim 10, wherein the openings of the syringe body are concentric.

14. The apparatus as recited in claim 10, wherein:
the syringe body extends along a longitudinal axis between the proximal and distal ends; and
the separator is configured to slide in opposite first and second directions along a transverse axis that extends perpendicular to the longitudinal axis.

15. The apparatus as recited in claim 10, wherein:
the syringe body extends along a longitudinal axis between the proximal and distal ends; and
the orifice is coaxial with the longitudinal axis when the separator is in the first position and the orifice is offset from the longitudinal axis when the separator is in the second position.

16. The apparatus as recited in claim 10, wherein side surfaces of the separator engage side surfaces of the tracks to prevent the separator from rotating relative to the mixing vessel.

17. The apparatus as recited in claim 10, wherein the orifice is circular.

18. The apparatus as recited in claim 1, further comprising a base configured to fit around the syringe body and attach to the mixing vessel so that the mixing apparatus can stand upright on a surface without the distal end of the syringe body contacting the surface.

19. The apparatus as recited in claim 1, further comprising a spatula configured to fit within the cavity for mixing bone cement therein.

20. A bone cement mixing apparatus comprising:
a mixing vessel comprising a body defining a cavity, the body comprising opposite first and second openings that are in communication with the cavity, the mixing vessel comprising a recessed track extending into an outer surface thereof;
a syringe body comprising opposite proximal and distal ends, the syringe body being attached to the mixing vessel, the syringe body comprising a lumen and opposite first and second openings that are in communication with the lumen; and
a separator slidably positioned in the track, the separator comprising an orifice, the separator being configured to slide between a first position wherein the orifice substantially aligns with the openings of the mixing vessel to a second position wherein the orifice is misaligned with the openings of the mixing vessel so as to block a passageway between the mixing vessel and the lumen,
wherein the syringe body extends along a longitudinal axis between the proximal and distal ends, the separator being configured to slide in opposite first and second directions along a transverse axis that extends perpendicular to the longitudinal axis.

\* \* \* \* \*